United States Patent [19]

O'Leary et al.

[11] Patent Number: 5,482,854
[45] Date of Patent: Jan. 9, 1996

[54] GROWTH ENVIRONMENT ASSEMBLY AND METHOD OF USE THEREOF

[75] Inventors: Robert K. O'Leary, Morris Plains; Paul J. LaRocca, Ringwood, both of N.J.

[73] Assignee: Becton, Dickinson and Company, Franklin Lakes, N.J.

[21] Appl. No.: 319,348

[22] Filed: Oct. 6, 1994

[51] Int. Cl.⁶ .................. C12M 3/00; C12M 1/24
[52] U.S. Cl. ............ 435/283.1; 422/102; 215/229; 215/247; 215/356; 435/288.1; 435/297.1; 435/297.2; 435/297.3; 435/304.3; 435/304.1
[58] Field of Search ................... 435/284, 285, 435/296, 310, 311; 422/102; 215/211, 214, 227, 228, 229, 247, 355, 356

[56] References Cited

U.S. PATENT DOCUMENTS

| | | | |
|---|---|---|---|
| 1,509,916 | 9/1924 | Waite | 422/102 |
| 3,313,712 | 4/1967 | George | 435/296 |
| 3,883,393 | 5/1975 | Knazek et al. | 195/1.8 |
| 4,024,857 | 5/1977 | Blecher et al. | 422/102 |
| 4,289,248 | 9/1981 | Lynn | 215/330 |
| 4,334,028 | 6/1982 | Carver | 435/284 |
| 4,387,822 | 6/1983 | Lynn | 215/330 |
| 4,720,384 | 2/1988 | DiLuccio et al. | 424/78 |
| 4,738,827 | 4/1988 | Pierotti | 422/104 |
| 4,770,854 | 9/1988 | Lyman | 422/102 |
| 4,839,292 | 6/1989 | Cremonese | 435/313 |
| 4,965,128 | 10/1990 | Greidanus et al. | 428/398 |
| 5,010,013 | 4/1991 | Serkes et al. | 435/285 |
| 5,047,347 | 9/1991 | Cline | 435/296 |
| 5,139,952 | 8/1992 | Honda et al. | 435/284 |
| 5,272,084 | 12/1993 | O'Connell et al. | 435/240.243 |
| 5,286,646 | 2/1994 | Kearns et al. | 435/240.24 |

Primary Examiner—David A. Redding
Attorney, Agent, or Firm—Nanette S. Thomas

[57] ABSTRACT

A method and assembly for treating living and non-living biological environments with varying doses of fluids in vitro. The assembly comprises a vessel, a closure and a tubular membrane extending from the closure and suspended into the vessel to provide rapid and uniform equilibration of fluids into the vessel. The assembly provides means for carrying out pharmacokinetic and toxicokinetic studies.

4 Claims, 6 Drawing Sheets

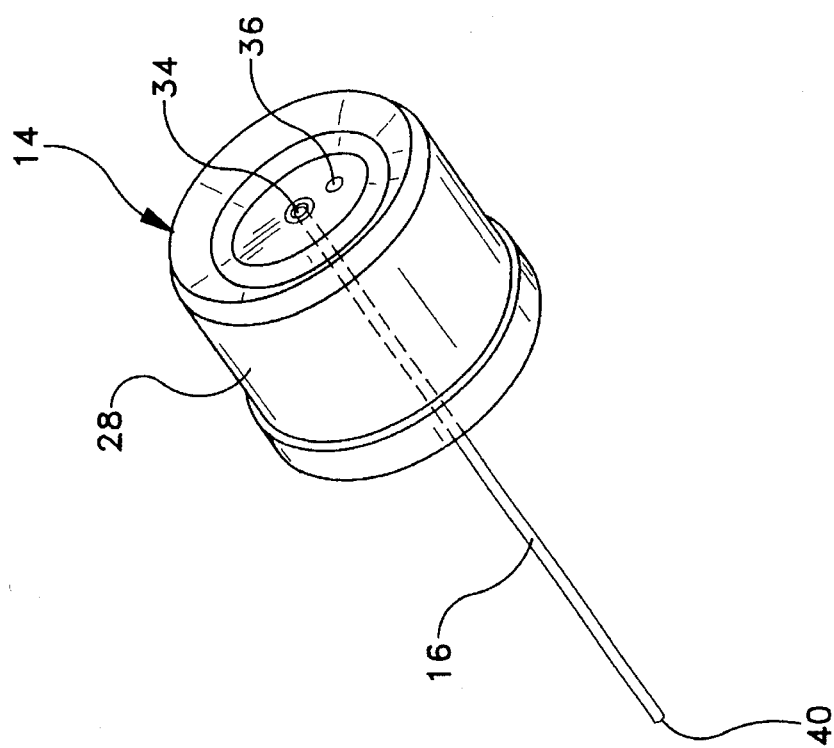
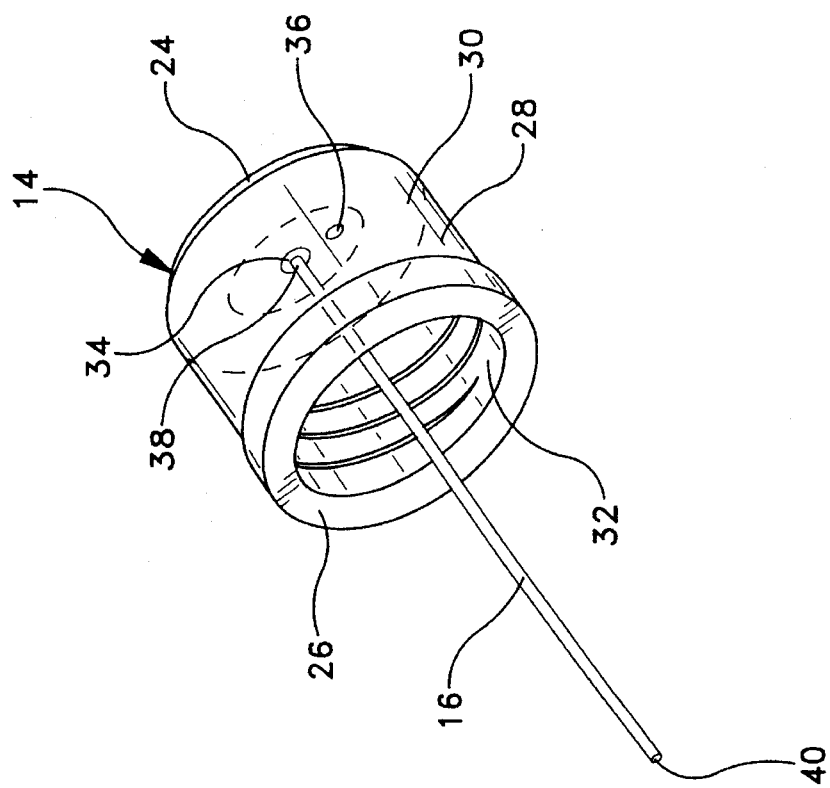

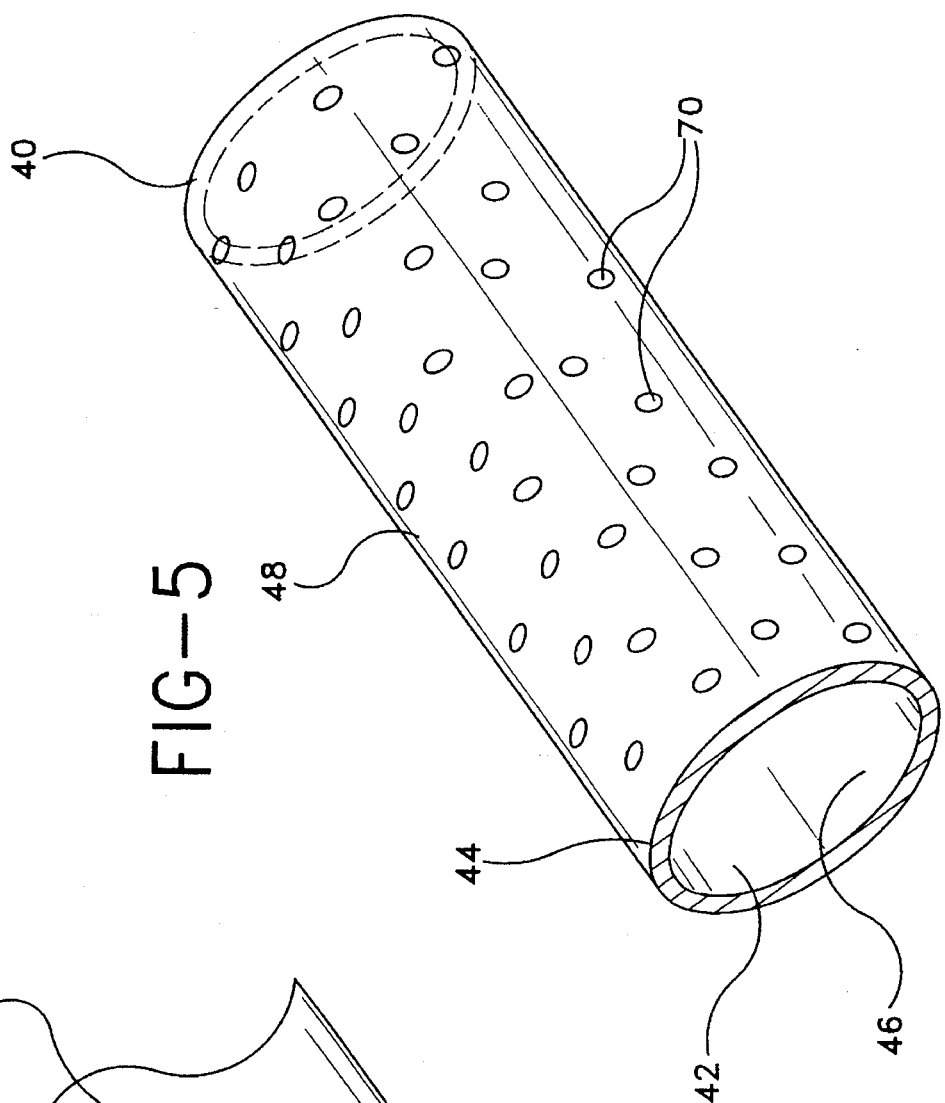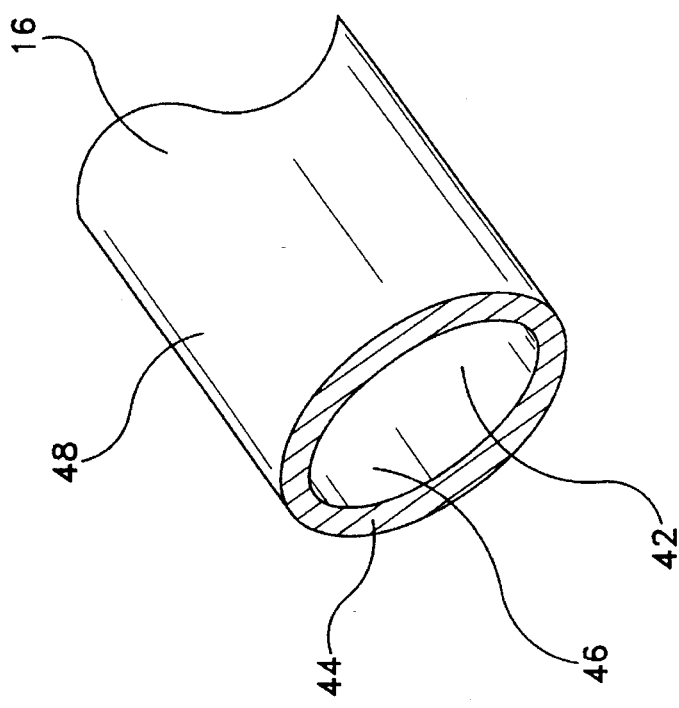

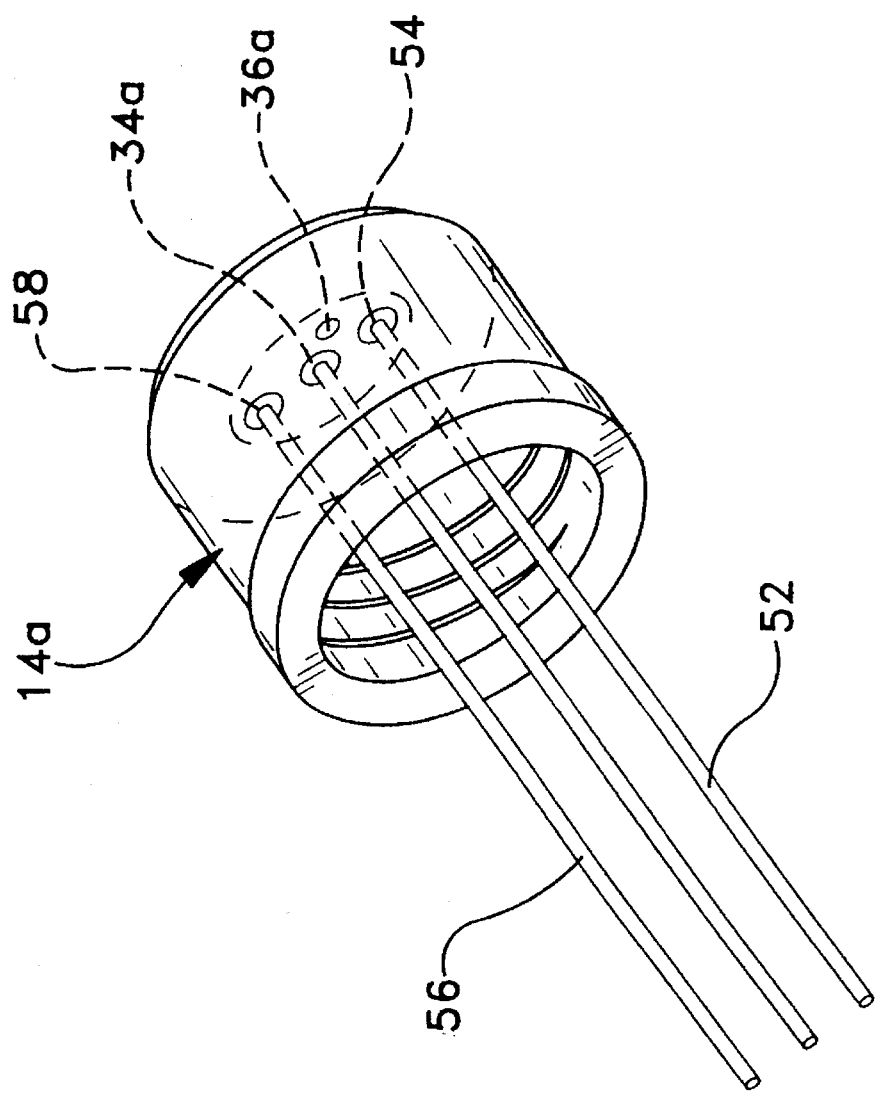

GROWTH ENVIRONMENT ASSEMBLY AND METHOD OF USE THEREOF

BACKGROUND OF THE INVENTION

1. Field of the Invention

This invention relates to a method and assembly for treating living and non-living biological environments with varying doses of fluids in vitro, and more particularly to a vessel and closure assembly having means for delivering fluids to cell lines and tissue cultures.

2. Description of Related Art

The use of in vitro cell lines and tissue cultures in carrying out pharmacokinetic and toxicokinetic studies related to safety evaluations of new drugs is a growing area of scientific development. By using cell lines and tissue cultures, the need for large animal studies is reduced.

Pharmacokinetic and toxicokinetic studies depend upon the control rate of drug delivery and dose of drug to a cell line for multiple drugs simultaneously. Repeated drug administration can influence the toxicity of the drug by changing its metabolism and stimulating the cell's synthesis of certain proteins that can effect the drug's activity on the cell line.

Current technologies for studying in vitro pharmacokinetics and toxicokinetics use either a closed monolayer culture system (MCS) or a dynamic perfused cell system (DPCS). The MCS employs an immediate total dose application of the test drug. Its limitation is that it operates in essentially a single dose range which can be toxic due to over dose.

On the other hand, the DPCS acts as an in vivo circulating model. The in vitro route of bolus administration does not mimic the in vivo method of drug administration since their are no tissue masses to act as the sustain release matrix.

A need exists for a delivery system in order to carry out in vitro pharmacokinetic metabolic pathway studies of drugs, proteins, growth factors and other such biologicals. The need arises because it is experimentally undesirable to deliver fluids, such as drugs to cell lines and tissue cultures in bolus concentrations. Bolus concentrations cause the pharmacological dose to quickly and uncontrollably extend into the toxicological range.

Therefore, a special need exists for a drug delivery system which permits the control of drug delivery and provides an assessment of drug concentration on cell lines and tissue culture environments so as to establish a correlation of drug action with adverse reactions.

Such a need for a new type of drug delivery system for treating biological environments has not been suggested or taught in the literature.

SUMMARY OF THE INVENTION

The present invention is a method and assembly for delivering fluids to living and non-living biological environments such as cell lines and tissue cultures.

Most preferably, the present invention is an assembly comprising a vessel and closure. Preferably, the closure comprises means for delivering fluids, such as drugs, proteins, growth factors and other such biologicals into the vessel. Most preferably, the means for delivering fluids into the vessel is a tubular membrane extending from the closure and suspended into the vessel.

The tubular membrane is attached to the closure in such a way to allow the membrane to be easily rotated inside the vessel. The tubular membrane is rotated so as to eliminate the media protein boundary layer resistance at the membrane surface. The rotation of the tubular membrane also facilitates stirring of the cell media in the vessel, therefore permitting linear steady state kinetics of fluid diffusion to proceed.

Preferably, the vessel is a flask, roller bottle, tube, spinner flask, stirred bioreactor or any vessel that will facilitate cell culture viability. Most preferably, the vessel is a flask or roller bottle. Vessels that are applicable to this invention include those described in U.S. Pat. Nos. 5,272,084; 4,770,854; 5,139,952; 4,334,028; 4,289,248; 4,387,822; and 5,047,347, which are incorporated by reference.

Desirably, the closure is a cap, push cap, threaded cap, screw cap or stopper.

Preferably, the top of the closure comprises an entry port from which the tubular membrane extends into the vessel. The tubular membrane comprises an open end and a closed end, wherein the open end is connected to the entry port of the closure and the closed end extends into the vessel. The tubular membrane comprises a hollow cavity containing the means to distribute fluid substances.

Most preferably the tubular membrane is tangentially attached to the closure and its mobility inside the vessel is brought about by rotating of the closure. This rotating motion of the tubular membrane provides bi-directional rotation at variable speed so as to produce less media protein boundary layer resistance at the outer surface of the tubular membrane. Protein boundary layers are complex and are heterogenous protein films which are readily deposited on membranes. The proteins are substantially released by turbulence at the surface of the membrane created by the rotating motion of the membrane and the closure.

Most notably, the assembly of the present invention provides a continuous controlled release of fluids which thereafter diffuse from the membrane and into the vessel. The present invention eliminates the delivery of bolus concentrations of fluids which causes the pharmacological dose to quickly and uncontrollably extend into the toxicological range.

The tubular membrane is an imperfect barrier separating two fluids and hinders free diffusion of a substance in an isotropic medium. Diffusion is the tendency of molecules to migrate from a region of high concentration (potential and/or activity) to a region of lower concentration (potential and/or activity).

The tubular membrane has the capability of delivering microspikes of drug when the membrane is rapidly rotated because the static diffusivity of the drug in the membrane is increased to a dynamic diffusivity because the exiting drug is carried away from the surface of the membrane thus eliminating back diffusion or stagnation at the outer surface of the membrane. Thus a new concentration gradient is established at the outer surface of the membrane. Sudden changes in the slope of the drug release curve such that the slope of release increases in a positive direction, and is quickly changed in a negative direction over a short time interval typically not exceeding a one to three minute total interval. A microspike delivers less than one percent of the total potential diffusate over the full course of diffusion.

The use of the assembly of the present invention permits the control of fluid delivery and concentration to cell lines and tissue cultures and permits the development of steady state drug diffusion for studying possible mechanisms for the passage of nutrients and drugs and for studying in vitro pharmacokinetic studies on living cells.

The present invention employs a monolayer and a hollow fiber system for sustain drug release of drugs and as such is a good model for studying drug dose response curves on tissue slices and/or cell populations and organ cultures.

The present invention provides important advances over methods used to perform pharmacokinetic and toxicokinetic studies. The assembly of the present invention provides the ability to maintain an in vitro culture system wherein the cells are subjected to an environment which permits them to function in a manner closely simulating that encountered in vivo. The invention also permits the efficient removal of desired products from the cells being cultured and provides important advantages in the efficiency, economy and flexibility of operation.

The present invention provides a leak-proof, serf-contained environment for the use ,-red safe disposal of infected cultures and dangerous toxicants.

The present invention can also be used for fluorescent tracing of drugs, radiolabeling and radiographic imaging of drugs and for supplementing basal media requirements with, for example, growth factors and hormones.

An alternate embodiment of the assembly of present invention comprises multiple tubular membranes attached to the closure and extending into the vessel so that more than one drug solute may be injected into the tubular membrane at one time or at varying time intervals.

A further advantage of the present invention include its use in drug therapy by providing quantitative evaluations of cell populations responding to drug therapy. Whereby, kinetic rate constants, activation energies, entropies and other basic pharmacological parameters can be evaluated. Another feature of the present invention is that metabolic substances such as uremic poisons can be delivered to cells for the purpose of investigating the effects of metabolites on in vitro cultured cells.

DESCRIPTION OF THE DRAWINGS

FIG. 2 is a perspective view of the cap and the tubular membrane of FIG. 1.

FIG. 3 is a top view of the cap and the tubular membrane of FIG. 2.

FIG. 4 is an isolated cross sectional view of a non-porous tubular membrane.

FIG. 5 is an isolated cross sectional view of a porous tubular membrane

FIG. 8 is a perspective view of the cap and at least two tubular membranes.

DETAILED DESCRIPTION

Figure 1:
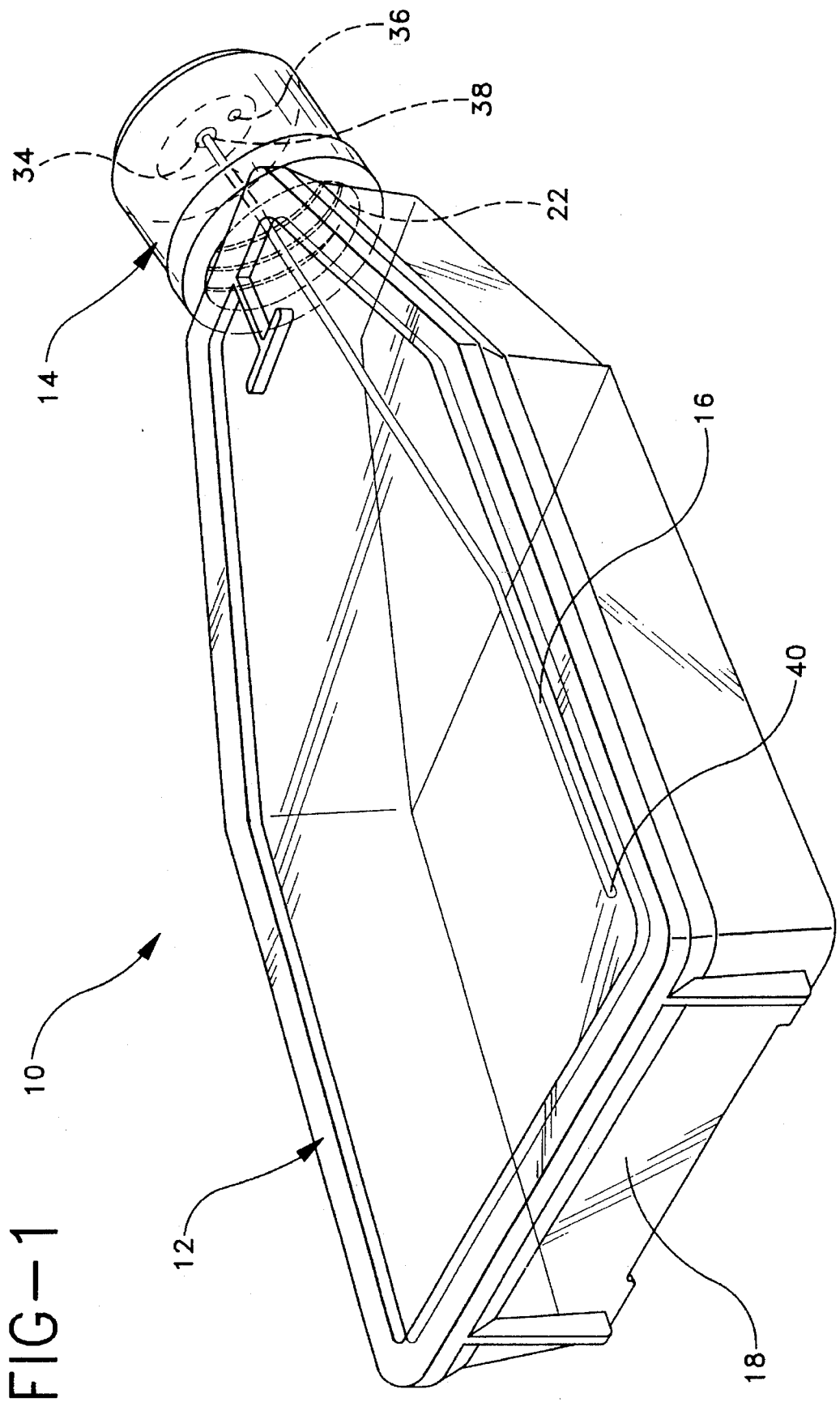
FIG. 1 is a perspective view of the growth environment assembly.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

FIG. 1 illustrates a growth environment assembly 10, comprising a vessel 12, a closure 14 and a tubular membrane 16. The vessel is preferably made from impact resistant plastic or glass which is gas impermeable, optically clear, non-toxic and inert with respect to the cells to be cultured.

Vessel 12 has a body 18 in which material is adapted to be held until such time as the same is withdrawn or dispensed. It is unimportant whether body 18 is made of a collapsible or no-collapsible material, such as metals, plastics or glass.

As shown in FIG. 1, vessel 12 includes a neck 22 to receive closure 14. Neck 22 is integral with the vessel and defines a cylindrical conduit having one end integral with the vessel and the other end defining an opening through which the cells and culture fluids may be introduced into the body of the vessel. Neck 22 and closure 12 constitute one of a number of well known means for introducing materials such as mammalian cells and culture fluids into body 18. As is conventionally know, closure 14 is removed from neck 22 to provide an opening through which cells and culturing fluids can be introduced into the vessel. The closure is subsequently remounted onto the neck to re-seal the vessel.

As shown in FIGS. 2 and 3, closure 14 has a top surface 24, a bottom stop ledge 26 and an annular outer skirt 28 extending from the top surface to the bottom stop ledge. The annular outer skirt has an outer wall surface 30 and an inner wall surface 32. The top surface of the closure further comprises entry port 34 and sampling port 36. Tubular membrane 16 extends from entry port 34 of the closure and into the vessel. As shown in FIG. 4, tubular membrane 16 comprises an open end 38, a closed end 40 and a hollow cavity 42 containing the means to distribute fluid substances. Tubular membrane 16 comprises a sidewall 44 that extends from open end 38 to closed end 40 and comprises an inner surface 46 and outer surface 48.

Most preferably, the top surface of the closure is a pierceable self sealing material whereby entry can be made into the tubular membrane through entry port 34 or into the vessel by sampling port 36 by means for example by a hypodermic needle so that fluids can be injected into the tubular membrane and/or added or removed from the vessel without breaking the environment of the vessel. After the needle is removed, the self sealing material immediately reseats. The material is most preferably an elastomeric material.

Tubular membrane 16 may be made from any suitable gas permeable material so long as it provides for the passage of fluids such as drugs and biological fluids into vessel 12. Preferably, the tubular membrane is made from a polymer or a dialysis material.

The diameter of the tubular membrane is about 150 micron to about 300 micron and most preferably about 150 microns um. The length of the tubular membrane is dependent on the size of the vessel being used.

Figure 6:
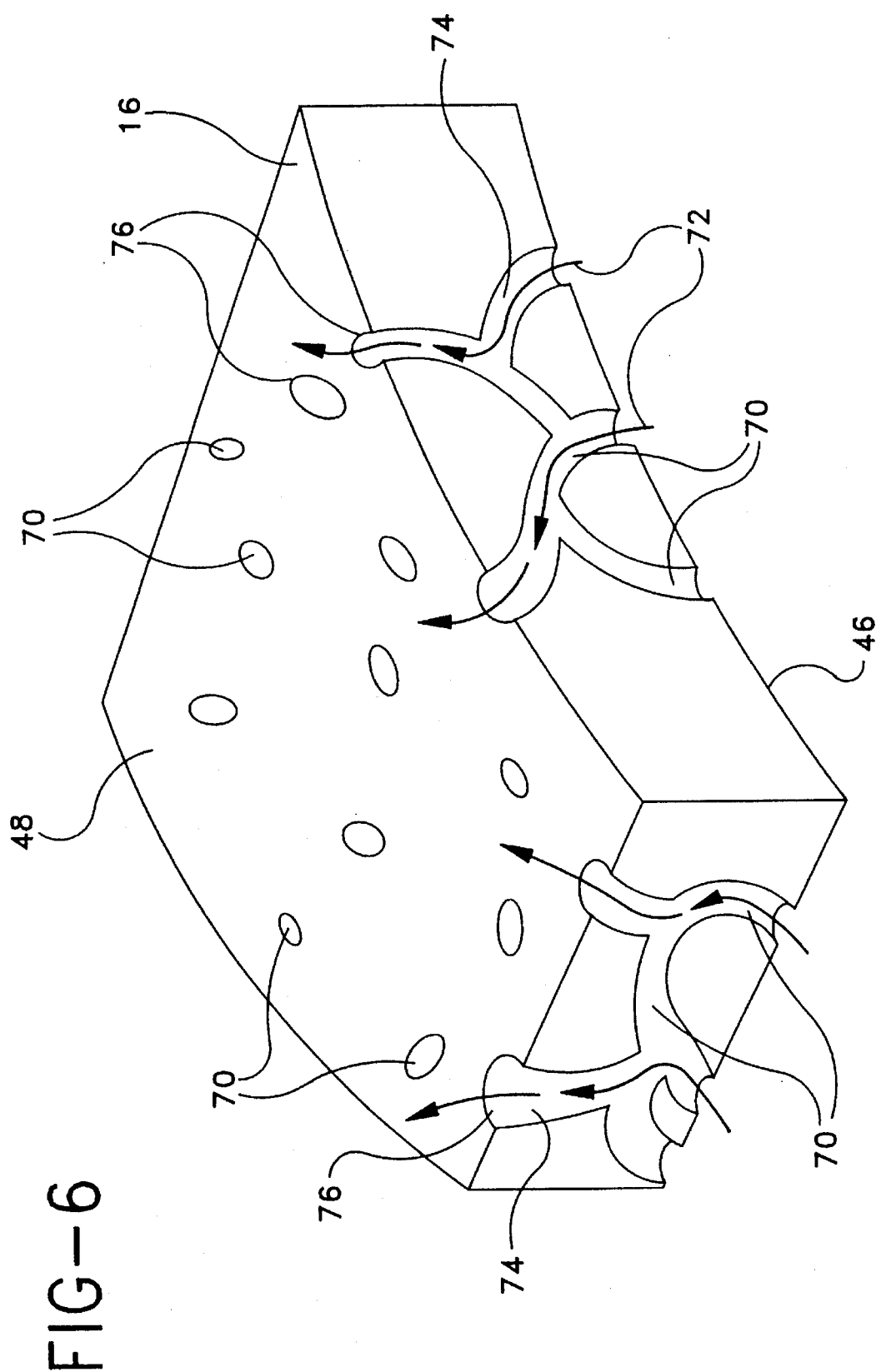
FIG. 6 is a cross sectional view of the porous tubular membrane of FIG. 5.

The passage of solute through the tubular membrane will occur by one of two primary mechanisms. Membranes, not having pores, such as these made from polyethylenteretholate (PET), as shown if FIG. 4, will permit diffusion by the solubization of the solute in the membrane. The second mechanism for the passage of a solute through a membrane having pores 70 of about 0.02, micron to about 2.0 micron and most preferably at about 0.5 microns as shown in FIG. 5, is by a tortuous path as further shown in FIG. 6. In the tortuous path, the Browian movement of the solute 72 causes it to enter the tortuous pore channel 74 and it thereby passes through the membrane and reaches an exit side 76 of the pore.

Priming volumes of about 0.25 ml to about 2.5 ml with macro fibers of about 2.5 ml to about 5.0 ml.

The solute permeability of the tubular membrane may be small, medium or large. An example of the solute permeability are as follows: (i) a small solute permeability is about 50 to about 5000 molecular weight (i.e., urea, or insulin); (ii) a medium size solute permeability is about 6000 to about 37,000 molecular weight (i.e., insulin, or heparin); and (iii) a large molecule permeability is about 150,000 antibodies.

An example of a commercially available tubular membrane is Accurel PP capillary membranes (trademark of AKZO, Germany). The Accurel PP capillary membranes that may be used in the present invention have the following characteristics:

| ACCUREL designation type | v8/2 | S6/2 |
|---|---|---|
| Polymer | Polypropylene | Polypropylene |
| Nominal pore size, um | 0.2 | 0.2 |
| Maximum pore size, um | ≦0.65 | ≦0.65 |
| Bubble point versus IPA, bar | ≧0.95 | ≧0.95 |
| Retention of pseudomania diminuta, log reduction value | ≧8 | ≧8 |
| Trans Membrane Flow (IPA 25° C.), ml/min cm² bar | ≧0.9 | ≧2.5 |
| Extractable (Armostat), ppm | ≦500 | ≦100 |
| Wall thickness (mean value), μm | 1500 | 450 |
| Range of Mean Value, μm | 1350–1650 | 380–520 |
| Inner diameter (mean value), μm | 5500 | 1800 |
| Range of Mean Value, μm | 5300–5700 | 1600–2000 |
| Implosion pressure (25° C.), bar | ≧2.5 | ≧8 |
| Burst pressure (25° C.), bar | ≧8 | ≧8 |

Figure 7:
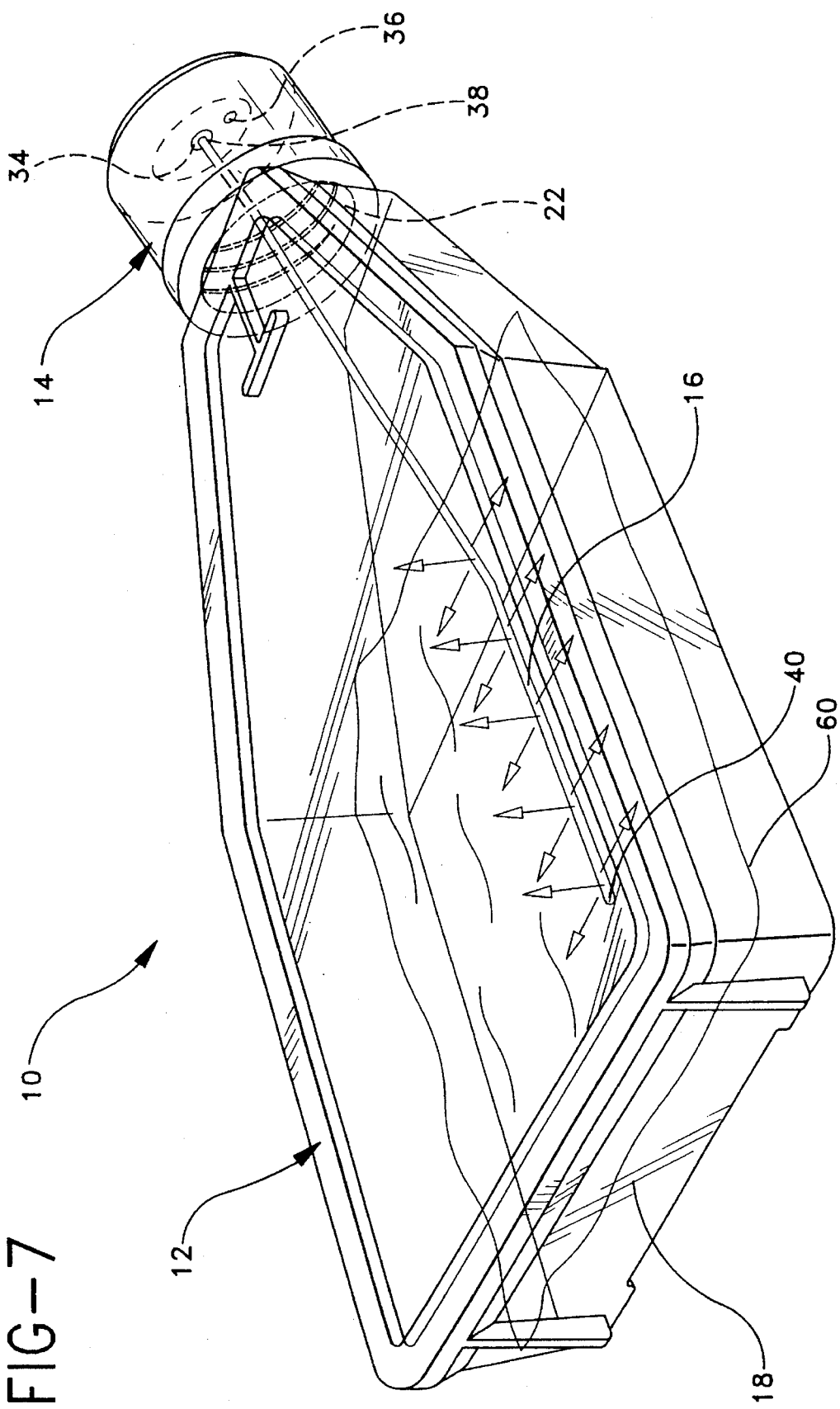
FIG. 7 illustrates the vessel in use with culture media and the diffusing of fluid through the tubular membrane.

The present invention in use, as shown in FIG. 7, a cell media 60 is injected into the vessel by the tubular membrane at the entry port by means of a syringe or the like. The closure and tubular membrane is rotated as the fluid is being delivered through the entry port, into the tubular membrane and thereafter it is distributed into the vessel. The closure is rotated to reduce media protein boundary at the outer surface of the tubular membrane and also to facilitate stirring of the cell media in the vessel. If desirable, further substances can be injected and/or withdrawn from the vessel through the sampling port, such as medium from the vessel for drug analysis.

The injectable feature of the tubular membrane permits the investigator to alter the kinetics of the tubular membrane diffusivity by pre-injecting the tubular membrane with surfactants to accelerate the drug release.

The tubular membrane may be used to distribute substances such as drugs, hormones, insecticides, phomones and repellents into the vessel. The tubular membrane provides a means for the controlled release of the active substances wherein the substrate consists of an asymmetric wall formed from polymers.

An alternate embodiment of the present invention as shown in FIG. 8, includes many components which are substantially identical to the components of FIGS. 1–3. Accordingly, similar components performing similar functions will be numbered identically to those components of FIGS. 1–3, except that a suffix "a" will be used to identify those similar components in FIG. 8.

Closure 14*a* as shown in FIG. 8 is an alternate embodiment of the closure that can be used with vessel 12. The alternate embodiment of the invention as shown in FIG. 8, is that a second tubular membrane 52 is attached to the top of the closure at a second entry port 54 and extending into the vessel and a third tubular membrane 56 is attached to the top of the closure at a third entry port 58 and extending into the vessel. Although FIG. 8 only shows three tubluar membranes, it is well within the purview of the invention to have more than three tubular membranes extending into the vessel and/or attached to the top of the closure.

Multiple drugs can be delivered simultaneously or sequenced for agonist or antagonistic effects. Typical uses could be changes in parameters such as temperature, different cells organisms, different gaseous environments, different media and additives.

What is claimed is:

1. An assembly for treating living and non-living biological environments comprising:
    a vessel comprising a chamber and a neck connected to said chamber having an opening for introducing cells and culture fluids into said chamber;
    a closure for coveting said opening in said neck comprising means for removably mounting said closure to said neck; and
    at least one tubular membrane for delivering fluids into said vessel through said closure wherein said tubular membranes comprise an open end, a closed end and a hollow cavity.

2. The assembly of claim 1 wherein said closure comprises a top portion, a bottom portion, an annular skirt extending from said top portion to said bottom portion and having an inner surface and outer surface and an entry port, whereby at least one tubular membrane for delivering fluids into said vessel is connected to said entry port.

3. The assembly of claim 2 wherein said top portion of said closure is a pierceable serf sealing material.

4. The assembly of claim 2 wherein said top portion of said closure further comprises a sampling port.

\* \* \* \* \*